US006303634B1

(12) United States Patent
Cohen et al.

(10) Patent No.: US 6,303,634 B1
(45) Date of Patent: Oct. 16, 2001

(54) METHODS OF PREVENTING BREAST CANCER

(75) Inventors: Fredric J Cohen; Robert S Eckert; Joan E Glusman; Ronald K Knickerbocker, all of Indianapolis, IN (US); Nikolaus T Nickelsen, Bad Soden (DE); Teri J Scott, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/368,688

(22) Filed: Aug. 5, 1999

Related U.S. Application Data

(63) Continuation of application No. 09/254,375, filed on Mar. 5, 1999, now abandoned, which is a continuation of application No. PCT/US97/19779, filed on Oct. 29, 1997.
(60) Provisional application No. 60/040,260, filed on Mar. 10, 1997, and provisional application No. 60/029,850, filed on Oct. 30, 1996.

(30) Foreign Application Priority Data

Nov. 29, 1996 (GB) .................................................. 9624800

(51) Int. Cl.$^7$ .................................................. A61K 43/40
(52) U.S. Cl. .......................................... 514/324; 514/333
(58) Field of Search ...................................... 518/324, 333

(56) References Cited

U.S. PATENT DOCUMENTS

| 4,418,068 | 11/1983 | Jones . |
| 4,656,187 | 4/1987 | Black et al. . |
| 5,472,962 | 12/1995 | Koizumi et al. . |
| 5,478,847 | 12/1995 | Draper . |
| 5,604,248 | 2/1997 | Bryant et al. . |
| 5,821,254 | 10/1998 | Sporn et al. . |

FOREIGN PATENT DOCUMENTS

| 652 004 A1 | 10/1994 | (EP) . |
| 674 903 A1 | 2/1995 | (EP) . |
| 680 758 A1 | 5/1995 | (EP) . |
| WO 96/22771 | 8/1996 | (WO) . |
| WO 97/35571 | 10/1997 | (WO) . |

OTHER PUBLICATIONS

Lerner L. J., et al., "Development of Antiestrogens and Their Use in Breast Cancer: Eighth Cain Memorial Award Lecture", Cancer Research, 50, pp. 4177–4189 (1990).

Jordan, V. Craig, *Journal of Cellular Biochemistry*, 58:S.22., 51–57 (1995), "Alternate Antiestrogens and Approaches to the Prevention of Breast Cancer".

Anzano, M.A., et al., *Journal of the National Cancer Institute*, 88:2, pp. 123–125 (1996) "Chemoprevention of Mammary Carcinogenesis in the Rat: Combined Use of Raloxifene and 9–Cis–Retinoic Acid".

"First Phase III Results with Raloxifene" Database File 129, Dialog Information Services; 540210, Jun. 13, 1997.

"Market Analysis from Decision Resources: Breast Cancer", Database File 187, Dialog Information Services, 1249, Apr. 1, 1996.

"National Chemopreventive Agents in Experimental Mammary Carcinogenesis", Anzano, Crisp Data Base National Institutes of Health, CRISP–96–PO57 (1995).

Caplus Abstract Accession No. 1996:122169 and J. Natl. Cancer Inst. (1996) 88 (2) pp. 123–125 (Anzano).

Biosis Abstract Accession No. 95:496471 and Breast Cancer Research and Treatment (1995) 36 (3) pp. 267–285 (Jordan).

Caplus Abstract Accession No. 1984:448784 and J. Med. Chem. (1984) 27 (8) pp. 1057–1066 (Jones).

Caplus Abstract Accession No. 1983–432846 and Life Science (1983) 32 (25) pp. 2869–2875 (Clemens).

*Primary Examiner*—Frederick Krass
(74) *Attorney, Agent, or Firm*—William R. Boudreaux; James J. Sales

(57) ABSTRACT

A method of preventing breast cancer comprising administering for a sufficient term to a human in need thereof an effective amount of a compound having the formula

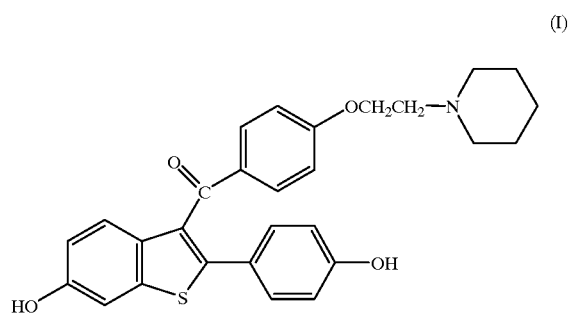

(I)

and pharmaceutically acceptable salts and solvates thereof.

38 Claims, 1 Drawing Sheet

METHODS OF PREVENTING BREAST CANCER

BACKGROUND OF THE INVENTION

This application claims the benefit and is a continuing application of U.S. application Ser. No. 09/254,375 filed Mar. 5, 1999, now abandoned, which is a continuation of International Application No. PCT/US97/19779 filed Oct. 29, 1997, which claims benefit of, U.S. Provisional Application No. 60/040,260, filed Mar. 10, 1997, and U.S. Provisional Application No. 60/029,850, filed Oct. 30, 1996.

Breast carcinoma or cancer is a major medical problem for women beginning in the third decade of life and continuing throughout senescence. It is currently estimated that in the United States women have a one in eight chance of developing the disease in their lifetime (by the age of eighty), whereas one in twenty-eight women have a lifetime risk of dying from breast cancer (Harris et.al., Ed. Diseases of the Breast, 1996: pp. 159–168). Carcinoma of the breast is the third most common cancer, and the most common cancer in women. It is a major cause of mortality in women, as well as a cause of disability, psychological trauma, and economic loss. Breast carcinoma is the second most common cause of cancer death in women in the United States, and for women between the ages of 15 and 54, the leading cause of cancer-related death (Forbes, Seminars in Oncology, vol.24(1), Suppl 1, 1997: pp.S1–20–S1–35). Indirect effects of the disease also contribute to the mortality from breast cancer including consequences of advanced disease, such as metastases to the bone or brain. Complications arising from bone marrow suppression, radiation fibrosis and neutropenic sepsis, collateral effects from therapeutic interventions, such as surgery, radiation, chemotherapy, or bone marrow transplantation-also contribute to the morbidity and mortality from this disease.

The epidemiology of this disease, although the subject of intense investigation, is still poorly understood. There appears to be a substantial genetic component which predisposes some women to contract the disease. Yet it is not clear whether this genetic component is causative or permissive to the disease, or only predictive of the disease process. Although it has been known for a long time that breast carcinoma tends to occur more frequently in some families, such analysis is not always predictive of disease occurrence in other family members and is of little value for prediction of its prevalence in the general population. It is currently estimated that only 5% of all breast cancers result from a genetic predisposition (Harris et.al., Ed. Disease of the Breast, 1996: pp.159–168).

Extensive clinical and pharmacological investigation has been conducted in the attempt to elucidate the relationship between the hormone estrogen, and the cause and maintenance of breast carcinoma. Risk factors for the disease are principally related to the duration of a woman's cumulative estrogen exposure and include: age at menarche, parity, age at the time of the first full-term pregnancy, and menopause. Although much is known about the relationship of estrogen in the maintenance of the disease and the importance of estrogen dependence with respect to endocrine treatment of the disease, there is considerable controversy over the role of estrogen in the pathogenesis of this disease, i.e., whether estrogen is a causative agent (initiator), or an obligatory co-factor (promotor) in the process of carcinogenesis.

Estrogen, which includes 17-β-estradiol, estrone, and their active metabolites, is a major sex-related hormone in women, but additionally, it appears to be an important homeostatic hormone in both men and women throughout their adult life. All humans have some level of endogenous estrogen. Yet the vast majority of people do not develop breast carcinoma, supporting a position that estrogen, per se, is not an initiator of carcinogenesis, such as is the case with a chemical or environmental carcinogen. Additionally, women, as they go through menopause with the consequent loss of endogenous ovarian estrogen production, do not experience a commensurate reduction in their risk of contracting this disease. In fact, apart from a personal history of breast cancer, age is the single greatest risk factor for developing this disease. Breast cancer is rare in women younger than age 20, but this risk increases rapidly with age. When compared with a 20-year-old woman's risk of developing breast cancer, a woman age 40 to 49 has a 40-fold increase in risk, a woman age 50 to 59 a 60-fold increase, and a woman over the age of 60 has a risk 90-fold higher than that of her younger counterpart (Forbes, Seminars in Oncology, vol.24(1), Suppl 1, 1997: pp.S1–20–S1–35).

Hormone replacement therapy (HRT) is often recommended for postmenopausal and peri-menopausal women to alleviate menopausal symptoms and reduce the risk of cardiovascular disease, osteoporosis, and other serious sequellae of long-term estrogen deficiency. However, because of well-accepted data on the direct effects of cumulative lifetime estrogen exposure and breast cancer risk, there is vigorous debate over the potential of hormone replacement to increase a woman's risk of developing breast carcinoma. While short-term HRT (less than 5 years) is associated with minimal or no increase in risk, epidemiologic studies and meta-analyses of long-term HRT use (between five and seven years) report increases in the risk of developing breast cancer of 35% to 75% (Grady et.al., Hormone Therapy to Prevent Disease and Prolong Life in Postmenopausal Women., *Ann Intern Med,* 117: pp.1016–1037, 1992).

Theories and evidence regarding the role of estrogen in the pathogenesis of this disease are complex. Experimental models of mammary carcinoma in rats require administration of a carcinogen for tumor induction (tumorigenesis), whereas estrogen behaves as a promoter (rather than an initiator) of this process. Ovariectomy, in these animal models, will interfere with this process of chemically-induced carcinogenesis. In humans, however, the timing of the carcinogenic event is unknown. What is known is that women who undergo premature menopause or medical or surgical oophorectomy before the age of 40, will have an approximately 50% reduction in breast cancer risk compared with women undergoing natural menopause at age 50 (Harris, et.al., Ed. Diseases of the Breast, 1996: pp.159–168). It is logical, therefore, that approaches for the prevention of breast cancer would target the reduction in lifetime estrogen exposure. This can be accomplished by pharmacologically-induced estrogen deprivation, through the administration of an agent which would block the production and/or action of estrogen anywhere along the hypothalamic-pituitary-gonadal axis. It is nevertheless problematic to extrapolate the probable success of preventing breast carcinoma, de novo or otherwise, with agents of this nature.

In contrast to the complex role of estrogen in the pathogenesis of this disease, and despite a continually evolving body of data, considerable advances have been made in our understanding of the effects of estrogen in the setting of established breast carcinoma. Estrogen is a growth factor to most breast carcinoma cells in the early stages of the disease. The rapidly dividing cells are sensitive to its effects through the estrogen receptor. It has also been established, although not well understood that, at some point during the course of this disease process, transformed (cancer) cells often lose their sensitivity to the promoting effects of estrogen. Eventually, a majority of carcinoma cells become independent of estrogen for growth and lose their responsiveness to hormonally based therapy, which broadly includes: the GNRH agonists, "anti-estrogens," progestins, and androgens.

Enormous benefit in the treatment of breast cancer has been achieved with the advent and widespread use of hormonally based therapeutic interventions. The most extensively used endocrine therapy is tamoxifen. The five-year survival rate for women with breast carcinoma has been dramatically improved with this therapy; however, no additional benefit or survival advantage is achieved by continuing therapy for more than five years. In fact, data indicate a decrease in disease-free survival as well as overall survival, with greater than five years tamoxifen use (NSABP B-14 Trial; Fisher et al. Five Versus More Than Five Years of Tamoxifen Therapy for Breast Cancer Patients With Negative Lymph Nodes and Estrogen Receptor-Positive Tumors, *J Natl Canc Inst,* vol.88)(21): pp.1529–1542, 1996). Unfortunately tamoxifen is also associated with significant adverse effects such as: a significantly increased incidence of venous thromboembolism, substantially increased incidence of vasomotor symptoms or hot flashes (in the range of 16–67%), cataract formation, and DNA-adduct formation which, although not clinically confirmed, still raises concerns about the potential for hepatocellular carcinoma (observed experimentally in animal models). The most serious event, however, is tamoxifen's estrogenic effect in the uterus which causes endometrial hyperplasia and a substantial increase in the incidence of endometrial carcinomas (a three to four-fold increase in risk after five years tamoxifen administration) (Goldhirsch et.al., Endocrine Therapies of Breast Cancer, *Sem in Onc,* vol.23(4), pp.494–505, 1996). For this reason and the lack of improvement in survival advantage with long-term tamoxifen use, tamoxifen therapy of longer than five years is now contraindicated.

Data suggest that with long-term tamoxifen exposure, breast tumor cells undergo alterations that cause them to develop resistance to its antiestrogenic effects, and alternatively respond to its estrogenic properties (Santen, Editorial: Long Term Tamoxifen Therapy: Can an Antagonist become an Agonist?, *J Clin Endo & Metab,* vol. 81(6), pp.2027–2029, 1996). Changes in any step in the estrogen receptor signaling pathway may be responsible for the mechanism of development of resistance to tamoxifen therapy, some of which do not cause cross-resistance to other hormonal therapies and some of which do result in complete unresponsiveness to endocrine therapy of any kind. One mechanism for tamoxifen resistance has been attributed to the gradual evolution of the carcinoma cells from estrogen dependence to estrogen independence (estrogen receptor positive cells become estrogen receptor negative). Thus, even with the most advanced available combinations of treatment modalities, (surgery, radiation, and/or chemotherapy), the long-term prognosis for patients is poor, especially when metastatic disease is present. Clearly, there is a great need for improved therapies and, perhaps most important, a critical need for the prevention of the disease in the first instance (de novo, or primary prevention).

Although tamoxifen has been extensively studied and proven efficacious in the setting of established disease, there have been no completed, large-scale, prospective placebo-controlled, clinical trials addressing the potential use of this compound for primary prevention of breast cancer. Studies do exist indicating that women with a history of carcinoma in one breast and treated with tamoxifen, have a decreased incidence of tumor occurrence in the contralateral breast. Although this could be interpreted as a type of prevention of the disease, it is not clear whether this is an anti-metastatic effect or a de novo inhibition of the disease. Understanding such a distinction in biological mechanism is very important in attempting to prevent de novo disease initiation in healthy women with no particular history or risk factor for breast carcinoma.

For the last decade it has been argued that "anti-estrogen" therapy, especially the use of tamoxifen, should be studied for its potential to prevent de novo breast carcinoma. However, partially because of the lack of evidence of a benefit, and the known and potential toxicities of tamoxifen, no prospective prevention trials have been conducted in healthy women. Recently, two such prevention trials have been proposed and each trial has been the subject of substantial controversy. As a result, the trial to be done in the United Kingdom was deemed to have an unfavorable risk-to-benefit ratio and was not undertaken. Similarly in Italy, safety concerns regarding the occurrence of endometrial cancers, mandated that tamoxifen prevention studies be conducted only in women who had undergone hysterectomies In the United States, however, such a trial was undertaken under the auspices of the National Cancer Institute. In recognition of the controversial analysis of such trials, and the enormous sample size otherwise required, the US trial is limited only to women who are at high risk of developing the disease and includes both pre- and post-menopausal women (young women must have had a risk assessment equivalent to that of a 60-year-old woman for study eligibility). The results of this trial will not be available for at least three years. (For further information regarding the arguments for the potential use of tamoxifen as a chemopreventive agent in breast carcinoma, clinical design, and definition of high risk potential; see: "Breast Cancer Prevention Study: Are Healthy Women Put at Risk by Federally Funded Research?", Transcript of the Hearing Before the Human Resources and Intergovernmental Relations Subcommittee of the Committee on Governmental Operations, House of Representatives of the One Hundred Second Congress, Second Session, Oct. 22, 1992 [ISBN 0-16-044316-4] and references and testimony cited therein).

Because the goal of disease prevention is to protect women from the carcinogenic event (or the occurrence of precancerous lesions) and the subsequent promotion or progression to invasive disease (cancer), prolonged use of a preventive therapeutic agent is necessary (Kelloff et.al. Approaches to the Development and Marketing Approval of Drugs that Prevent Cancer, Cancer *Epidemiology, Biomarkers & Prevention,* vol 4, pp.1–10, 1995). This would require the therapy to be extremely well-tolerated, with an exceptional safety profile and minimal side effects. Raloxifene has been studied in more than 12,000 subjects. Extensive integrated data from Phase III clinical trials of raloxifene for the prevention or treatment of osteoporosis in postmenopausal women, has been analyzed for safety. When all doses of raloxifene are integrated, this analysis has included more than 12,850 patient-years of exposure to raloxifene. Raloxifene has been proven to be extremely well-tolerated, to have a wide therapeutic index, and to have minimal evidence of acute or chronic toxicity, based on nearly 3 years of clinical experience. The adverse effects associated with long-term tamoxifen use, in comparison, raise significant concerns over its suitability for use as a chemopreventive agent (Grainger et.al. Tamoxifen: Teaching an Old Drug New Tricks, *Nat Med,* vol.2(4), pp.381–385, 1996).

To date, there is no demonstrated, effective prevention therapy for de novo breast carcinoma. Further, there are no investigations in progress or contemplated for preventing breast carcinoma in women in the general population who are at no particular increased risk of developing breast cancer. Clearly, a great need exists for a breast cancer prevention therapy useful for the entire population, including individuals at high risk, as well as individuals at no particular increased risk, and including both men and women.

The current invention provides methods for the prevention of breast cancer, including de novo breast cancer.

SUMMARY OF THE INVENTION

The invention is directed to a method for preventing breast cancer in a human which comprises administering to said human for a sufficient term an effective dose of a compound of the formula

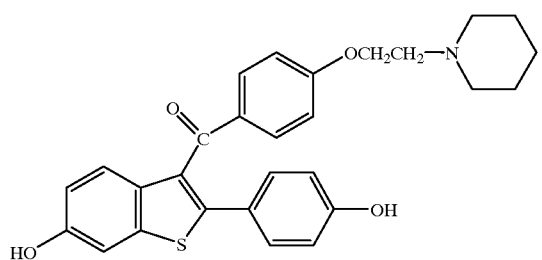

(I)

or a pharmaceutically acceptable salt or solvate thereof.

Further, the invention relates to articles of manufacture which comprise packaging material and a pharmaceutical agent contained within said packaging material, where the packaging material includes a label which indicates the pharmaceutical agent may be administered for preventing breast cancer, where the pharmaceutical agent is a compound of formula I or a pharmaceutical acceptable salt or solvate thereof.

DETAILED DESCRIPTION OF THE INVENTION

Figure 1:
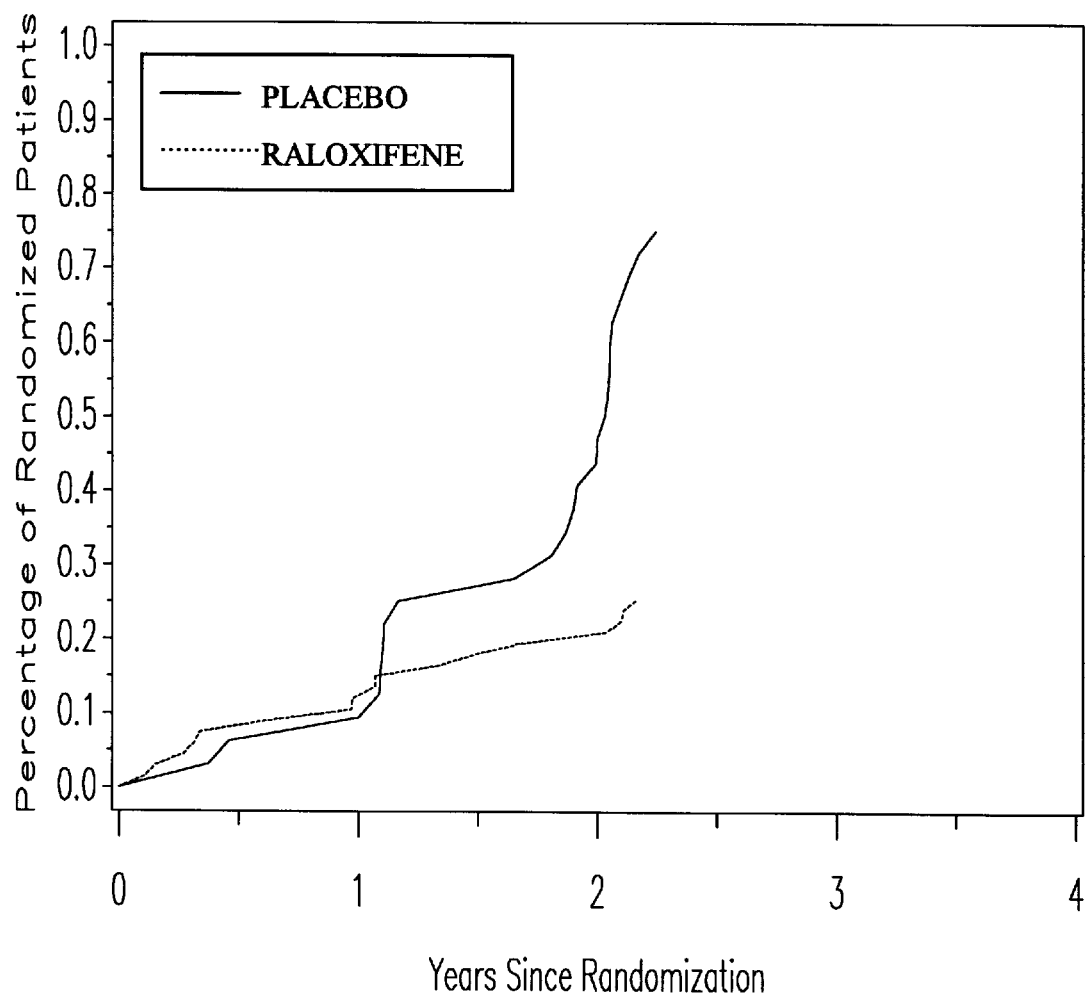
FIG. 1 depicts the percentage incidence of breast cancer in placebo and Raloxifene hydrochloride treated patients in placebo-controlled studies.

The current invention concerns the discovery that compounds of formula I are useful for preventing breast cancer. The methods provided by this invention are practiced by administering to a human in need thereof a dose, for a sufficient term, of raloxifene or a pharmaceutically acceptable salt or solvate thereof, that is effective to prevent breast cancer.

The term "prevent", when used in conjunction with breast cancer, includes reducing the likelihood of a human incurring or developing breast cancer. The term does not include treating a patient diagnosed with breast cancer.

The term "de novo", as used in the current invention, means the lack of transformation or metamorphosis of normal breast cells to cancerous or malignant cells in the first instance. Such a transformation may occur in stages in the same or daughter cells via an evolutionary process or may occur in a single, pivotal event. This de novo process is a process distinct from that of metastasis, colonization, or spreading of already transformed or malignant cells from the primary tumor site to new locations. The term "de novo" is associated with primary prevention. This invention also relates to the administration of a compound of formula I to a patient who is at increased risk of developing breast cancer, de novo or otherwise.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of breast cancer, even when there is no evidence of residual disease, a person is 5 years or more beyond treatment for the disease, and the person is considered a "breast cancer survivor". Another well-accepted risk factor is family history of the disease.

Raloxifene, which is the hydrochloride salt of the compound of formula 1, has been shown to bind to the estrogen receptor and was originally thought to be a molecule whose function and pharmacology was that of an "anti-estrogen". Indeed, raloxifene does block the action of estrogen in some tissues; however in others, raloxifene activates the same genes as estrogen, displays similar pharmacology, and behaves as an estrogen agonist, for instance in the skeleton and on serum lipids. The unique profile which raloxifene displays and differs from that of estrogen, and other "anti-estrogens", is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally or intravaginaly, and may be formulated as sustained release dosage forms, parenteral forms, depo forms, and the like.

The compounds used in the methods of the current invention can be made according to established procedures, such as those detailed in U.S. Pat. Nos. 4,133,814, 4,418, 068, 4,380,635, 5,629,425, U.K. Patent Application GB 2,293,602, published Mar. 3, 1996, European Patent Application 95301291, filed Feb. 28, 1995, published Sep. 6, 1995, and PCT application PCT/US97/04259 having an international filing date of Mar. 20, 1997, and a publication date of circa Sep. 26, 1997 all of which are incorporated by reference herein. In general, the process starts with a benzo[b]thiophene having a 6-hydroxyl group and a 2-(4-hydroxyphenyl) group. The hydroxyl groups of the starting compound are protected, the three position is acylated, and the product deprotected to form the formula I compounds. Examples of the preparation of such compounds are provided in the U.S. patents and UK application, discussed above.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular effective and sufficient term and dosage of a compound of formula I required to prevent breast cancer, according to this invention will depend upon the patient's physical characteristics, the route of administration, and related factors that will be evaluated by the attending physician. A preferred term of administration is at least six months, more preferred is at least one year, and most preferred is at least two years, or chronically. Generally, accepted and effective daily doses will be from about 0.1 to about 1000 mg/day, and preferably from about 30 to about 200 mg/day, and more preferably from about 50 to about 150 mg/day. A most preferred dosage range is between about 60 and about 120 mg/day, with 60 mg/day particularly preferred.

The dosage ranges described are not meant to limit the invention. Rather, the ranges illuminate the invention, and the invention encompasses those ranges which are functionally equivalent by providing the discovered chemopreventative characteristics of the compound. Therefore, while certain modes of administration may allow for a literally different dosage range of the compound of formula I to be used effectively per the invention, such literally different dosage ranges, as it is functionally equivalent to the expressed ranges, are encompassed by the invention.

Further, the dosage ranges delineated are based on the hydrochloride salt of the compound of formula I. Therefore, the 60 mg dose is equivalent to 55.71 mg of the free base. One of ordinary skill in the art will be able to calculate the free base equivalent of any salt of a compound of formula I which is pharmaceutically acceptable. For example, "about 60 mg" would encompass 55 to 65 mg of raloxifene hydrochloride, while encompassing 51.73 to 60.35 mg of the free base.

It is also advantageous to administer a compound by the oral route. For such purposes the following oral dosage forms are available.

Formulations

Formulation 1: Gelatin Capsules
Hard gelatin capsules are prepared using the following:

| Ingredient | Quantity (mg/capsule) |
| --- | --- |
| Raloxifene HCL | 30–200 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of capsule formulations include those shown below:

| Formulation 2: Raloxifene capsule | |
|---|---|
| Ingredient | Quantity (mg/capsule) |
| Raloxifene HCL | 30–200 |
| Starch, NF | 112 |
| Starch flowable powder | 225.3 |
| Silicone fluid 350 centistokes | 1.7 |

| Formulation 3: Raloxifene capsule | |
|---|---|
| Ingredient | Quantity (mg/capsule) |
| Raloxifene HCL | 30–200 |
| Starch, NF | 108 |
| Starch flowable powder | 225.3 |
| Silicone fluid 350 centistokes | 1.7 |

| Formulation 4: Raloxifene capsule | |
|---|---|
| Ingredient | Quantity (mg/capsule) |
| Raloxifene HCL | 30–200 |
| Starch, NF | 103 |
| Starch flowable powder | 225.3 |
| Silicone fluid 350 centistokes | 1.7 |

| Formulation 5: Raloxifene capsule | |
|---|---|
| Ingredient | Quantity (mg/capsule) |
| Raloxifene HCL | 30–200 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

| Formulation 6: Tablets | |
|---|---|
| Ingredient | Quantity (mg/tablet) |
| Raloxifene HCL | 30–200 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

| Formulation 7: Tablets | |
|---|---|
| Ingredient | Quantity (mg/tablet) |
| Raloxifene HCL | 30–200 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

| Formulation 8: Suspensions | |
|---|---|
| Ingredient | Quantity (mg/5 ml) |
| Raloxifene HCL | 30–200 |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Preferred tablet formulations include the following two:

| Formulation 9: | | |
|---|---|---|
| Ingredient | Quantity (mg) | Function |
| Raloxifene HCL | 60.0 | Active |
| Spray Dried Lactose | 30.0 | Soluble Diluent |
| Anhydrous Lactose | 12.0 | Soluble Diluent |
| Povidone | 12.0 | Binder |
| Polysorbate 80 | 2.4 | Wetting Agent |
| Crospovidone | 14.4 | Disintegrant |
| Magnesium Sterate | 1.2 | Lubricant |
| (Core Tablet Weight | 240.0) | |
| Film Coating | | |
| Color Mixture White | 12.0 | Coloring Agent |
| Talc | trace | Polishing Aid |
| Carnauba Wax | — | Polishing Aid |

| Formulation 10: | | |
|---|---|---|
| Ingredient | Quantity (mg) | Function |
| Raloxifene HCL | 60.0 | Active |
| Spray Dried Lactose | 29.4 | Soluble Diluent |
| Anhydrous Lactose | 120.0 | Soluble Diluent |
| Povidone | 12.0 | Binder |
| Polysorbate 80 | 2.4 | Wetting Agent |
| Crospovidone | 14.4 | Disintegrant |
| Magnesium Sterate | 1.2 | Lubricant |
| (Core Tablet Weight | 240.0) | |
| Film Coating | | |
| Color Mixture White | 12.0 | Coloring Agent |
| Talc | — | Polishing Aid |
| Carnauba Wax | trace | Polishing Aid |

Test Procedure

As support for the utility of the current invention, the interim safety results of Phase III clinical trials with raloxifene are presented, below.

The majority of cases of breast carcinoma have occurred in the large, ongoing osteoporosis treatment study of 7704 postmenopausal women with established osteoporosis. However additional cases have been reported in smaller studies of postmenopausal women at risk for osteoporosis. The studies reported herein are double-blind and placebo-controlled; most have durations of approximately three years and were designed to determine the efficacy of raloxifene to prevent or treat osteoporosis in postmenopausal women. In addition, the studies provide information on the status of cardiovascular health and other major medical conditions (including the incidence of breast carcinoma). Patients were randomly assigned to receive either placebo, 30 mg, 60 mg, 120 mg or 150 mg of drug per day, orally. All patients and investigators are blinded to study drug assignment (double-blind design). All patients in all groups received daily calcium supplements of approximately 500 mg/day. In addition, patients in the large, 7704-patient treatment study received Vitamin D supplements, 400–600 IU/day.

Subjects selected for these studies are postmenopausal women (at least 2 years from the time of the last menstrual period), ages range from approximately forty-five to eighty years.

Typical exclusion criteria from participation in these studies included: 1)the presence of serious systemic disease, 2)acute or chronic liver disease, 3)substantially impaired kidney function, 4)subjects who, in the opinion of the investigator, have poor medical or psychiatric risk factors for inclusion in a clinical trial, e.g., drug or alcohol abuse, etc. 5)subjects with any history of cancer within five years of entry into the study, with the exception of superficial lesions, e.g., basal cell carcinoma of the skin 6)the presence of abnormal uterine bleeding. Most important of the exclusion criteria was the exclusion of women with present or past personal history of breast cancer or other estrogen-dependent neoplasia. These exclusion criteria generate a population of subjects which reflects the general population in regard to the risk of developing breast carcinoma, or in other words, those persons at no particular increased risk of developing breast cancer.

Potential subjects were screened prior to enrollment into the study. Subjects were required to reveal their medical histories and current medical conditions. All potential patients were required either to have a baseline mammogram or ultrasound evaluation of the breast, or to have had one of these procedures in the 12-month period preceding study entry. In most studies, a two-year follow-up mammogram is required; however, annual mammograms are recommended. All subjects with diagnosed and reported carcinomas of the breast were required to discontinue immediately from study participation, and were referred by the site investigator for appropriate oncologic evaluation and care.

For all placebo-controlled trials of at least 6 months duration and in all subjects receiving more than 1 month of treatment with a study drug, a total of 42 breast cancer cases were reported: 24 cases were observed in the placebo group compared with 18 in the raloxifene treatment groups. The overall ratio of treatment assignments for randomized patients (raloxifene to placebo) is approximately 2:1.

The results shown in Tables 1–4 are for subjects with histopathologic diagnoses of carcinoma of the breast. The data include results from optional one year mammograms, as well as the required baseline and two year follow-up mammograms. Once a diagnosis of breast cancer was made, these subjects were discontinued from the study and their status decoded to reveal the therapy (arm) to which they been assigned (i.e. what study drug they had received).

For the studies reported in this invention, the number of patients randomly assigned to receive placebo is approximately 3195. The number of patients randomly assigned to receive raloxifene (all doses combined) is approximately 6681. (In the large, 7704-patient treatment study, the therapy codes have not been revealed for the patients who remain enrolled in the study. Therefore, the number of patients assigned to each therapy group is an estimation.)

The results shown below are for patients who were diagnosed to have breast carcinoma at any time during the study, but at least one month after being randomly assigned to study medication (placebo or raloxifene). Table 1 presents the results for all placebo-controlled studies, with data for all doses of raloxifene pooled. Table 2 presents a subset of the cases presented in Table 1, specifically the patients enrolled in the large, 7704-patient treatment study, in which most of the cases of breast cancer have occurred. The two raloxifene doses in this treatment study are 60 mg/day and 120 mg/day. Since the incidence of breast cancer increases with age, it is expected that the treatment study would have a higher incidence of breast cancer [mean patient age of 67 years at study entry]. The tables present the number of cases of breast cancer (n) for each treatment group, the total number patients assigned to that treatment (N), an estimate of the relative risk for developing breast cancer, and a 95% confidence interval for the relative risk of developing breast cancer. Note that if the upper limit of the 95% confidence interval is less than 1.0, then there is statistically significant evidence (at the 5% level) that the incidence of breast cancer on raloxifene is less than the incidence of breast cancer on placebo.

TABLE 1

Analysis of Relative Risk of Breast Cancer
All Placebo-Controlled Studies Combined

| Time from Therapy Assignment to Diagnosis | Placebo Cases n/N (%) | Raloxifene Cases n/N (%) | Relative Risk (Raloxifene to Placebo) | 95% Confidence Interval for Relative Risk |
|---|---|---|---|---|
| At least 1 month | 24/3195 | 18/6681 | 0.36 | (0.20, 0.64) |
| At least 12 months | 21/3195 | 10/6681 | 0.23 | (0.11, 0.45) |

TABLE 2

Analysis of Relative Risk of Breast Cancer
Large (7704-patient) Treatment Study
Of Postmenopausal Women with Established Osteoporosis

| Time from Therapy Assignment to Diagnosis | Placebo Cases n/N (%) | Raloxifene Cases n/N (%) | Relative Risk (Raloxifene to Placebo) | 95% Confidence Interval for Relative Risk |
|---|---|---|---|---|
| At least 1 month | 21/2659 | 12/5317 | 0.29 | (0.15, 0.55) |
| At least 12 months | 18/2659 | 5/5317 | 0.14 | (0.06, 0.32) |

In these placebo-controlled studies, the data clearly indicate that patients randomly assigned to raloxifene have a decreased incidence of breast cancer compared with patients randomly assigned to placebo. The estimate of crude relative risk for all patients diagnosed at least one month after random assignment to study drug is 0.36, with a 95% confidence interval (0.20, 0.64), indicating a 64% decrease in the rate of breast cancer. When the large treatment study is considered alone, the estimate of crude relative risk is 0.29, with 95% confidence interval (0.15, 0.55), indicating a 71% decrease in the rate of breast cancer. These results are highly statistically significant.

Because cancers diagnosed at least 1 year after randomization are most likely to represent cancers that were not clinically pre-existing, we have also analyzed the data considering only cases which occurred at least 12 months after randomization to study drug. For all placebo-controlled studies combined, the crude relative risk estimate is 0.23, with a 95% confidence interval (0.11, 0.45), corresponding to a 77% decrease in the incidence of breast cancer. For the large treatment study, the estimate of crude relative risk is 0.14, with a 95% confidence interval (0.06, 0.32), corresponding to a 86% decrease in the incidence of breast carcinoma.

To further analyze the appearance of tumors with respect to length of time in the study, Tables 3 and 4 present the relative risk data, which are divided into three time periods: 1) cases diagnosed from follow-up of baseline mammograms, i.e., all cases diagnosed between 1 and 6 months after study drug assignment; 2) cases diagnosed from follow-up of 1-year mammograms, i.e., all cases diagnosed between 6 and 18 months after study drug assignment; and 3) cases diagnosed from follow-up of 2-year mammograms i.e., all cases diagnosed between 18 and 30 months after study drug assignment.

Table 3 presents the relative risk of breast cancer for each time period for all placebo-controlled studies combined. Table 4 presents the information for a subset of patients reported in Table 3, namely, the patients in the large, 7704-patient treatment study. In both tables, it is evident that the relative risk of developing breast carcinoma decreases with each successive follow-up time period. The relative risk for both populations achieves statistical significance at the two-year follow-up time point.

TABLE 3

Annual Relative Risk of Breast Cancer
All Placebo-Controlled Studies Combined [a]

| Mammograms[c] | Placebo Cases | Raloxifene Cases | Relative Risk | 95% Confidence Interval for Relative Risk |
|---|---|---|---|---|
| Baseline (1–6 months) | 2 | 5 | 1.20 | (0.23, 6.15) |
| 1-Year Follow-up (6–18 months) | 6 | 7 | 0.56 | (0.19, 1.63) |
| 2-year Follow-up (18–30 months) | 16 | 5 | 0.15 | (0.06, 0.36) |

[a] Randomization-Raloxifene:Placebo is 2.1:1
[b] One patient who had a breast carcinoma diagnosed after 30 months is excluded from this analysis by time categories.

TABLE 4

Annual Relative Risk of Breast Cancer
Large (7704-patient) Treatment Study [a]
Of Postmenopausal Women with Established Osteoporosis

| Mammograms | Placebo Cases | Raloxifene Cases | Relative Risk | 95% Confidence Interval for Relative Risk |
|---|---|---|---|---|
| Baseline (1–6 months) | 2 | 5 | 1.25 | (0.24, 6.42) |
| 1-Year Follow-up (6–18 months) | 6 | 4 | 0.33 | (0.10, 1.11) |
| 2-year Follow-up (18–30 months) | 13 | 3 | 0.12 | (0.04, 0.33) |

[a] Randomization-Raloxifene:Placebo is 2.1:1

As a final summary, FIG. 1 graphically presents the incidence of breast cancer in all placebo-controlled studies. (One patient who had a breast carcinoma diagnosed after 30 months is excluded from this graph, so that the graph represents approximately the same follow-up period in both treatment groups.) The two curves (placebo and raloxifene) are almost indistinguishable until the 1-year time point, when they become divergent, with breast cancer occurrences in the placebo group increasing at a greater rate than that seen with raloxifene.

We claim:

1. A method for prophylacting against breast cancer in a human in need thereof which comprises administering to said human for a sufficient term an effective dose of a compound of the formula (I)

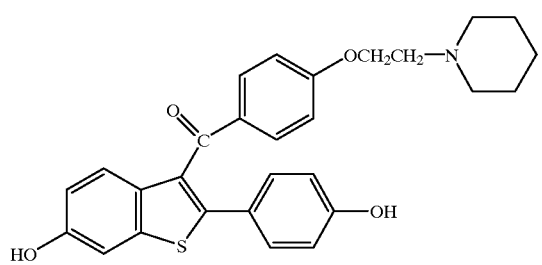

or a pharmaceutically acceptable salt or solvate thereof; said term being at least one year.

2. The method of claim 1 wherein said effective dose is between about 30 mg to about 200 mg/day.

3. The method of claim 1 wherein said effective dose is between about 50 mg to about 150 mg/day.

4. The method of claim 1 wherein said effective dose is between about 60 mg to about 120 mg/day.

5. The method of claim 1 wherein said effective dosage is about 60 mg/day.

6. The method of claim 1 wherein said term is at least two years.

7. The method of claim 1 wherein said term is chronic.

8. The method of claim 1 wherein said compound is the hydrochloride salt thereof.

9. The method of claim 1 where said breast cancer is de novo.

10. The method of claim 1 wherein said human is a post-menopausal female.

11. A method for prophylacting against breast cancer in a post-menopausal human female in need thereof which comprises administering to said post-menopausal human female for a sufficient term an effective dose of a compound of the formula

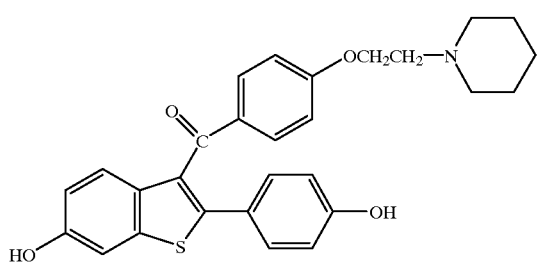

(I)

or a pharmaceutically acceptable salt or solvate thereof; said term being at least one year.

12. The method of claim 11 wherein said effective dose is between about 30 mg to about 200 mg/day.

13. The method of claim 11 wherein said effective dose is between about 50 mg to about 150 mg/day.

14. The method of claim 11 wherein said effective dose is between about 60 mg to about 120 mg/day.

15. The method of claim 11 wherein said effective dosage is about 60 mg/day.

16. The method of claim 11 wherein said term is at least two years.

17. The method of claim 11 wherein said term is chronic.

18. The method of claim 11 wherein said compound is the hydrochloride salt thereof.

19. The method of claim 11 where said breast cancer is de novo.

20. An article of manufacture comprising packaging material and a pharmaceutical agent contained within said packaging material, wherein said packaging material comprises a label which indicates said pharmaceutical agent may be administered, for a sufficient term at an effective dose, said term being for at least one year, for prophylacting against breast cancer in a human and wherein said pharmaceutical agent is a compound of formula I

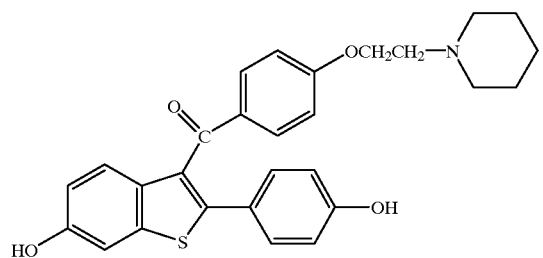

(I)

or a pharmaceutically acceptable salt or solvate thereof.

21. An article of manufacture of claim 20 wherein said label indicates an effective dose of the compound of formula I is between about 30 mg to about 200 mg/day.

22. An article of manufacture of claim 20 wherein said label indicates an effective dose of the compound of formula I is between about 50 mg to about 150 mg/day.

23. An article of manufacture of claim 20 wherein said label indicates an effective dose of the compound of formula I is between about 60 mg to about 120 mg/day.

24. An article of manufacture of claim 20 wherein said label indicates an effective dosage of the compound of formula I is about 60 mg/day.

25. An article of manufacture of claim 20 wherein said label indicates the term of administration is at least two years.

26. An article of manufacture of claim 20 wherein said label indicates the term of administration is chronic.

27. An article of manufacture of claim 20 wherein said compound is the hydrochloride salt thereof.

28. An article of manufacture of claim 20 where said breast cancer is de novo.

29. An article of manufacture of claim 20 wherein said human is a post-menopausal female.

30. An article of manufacture comprising packaging material and a pharmaceutical agent contained within said packaging material, wherein said packaging material comprises a label which indicates said pharmaceutical agent may be administered, for a sufficient term and at an effective dose, said term being for at least one year, for prophylacting against breast cancer in a post-menopausal human female wherein said pharmaceutical agent is a compound of formula I

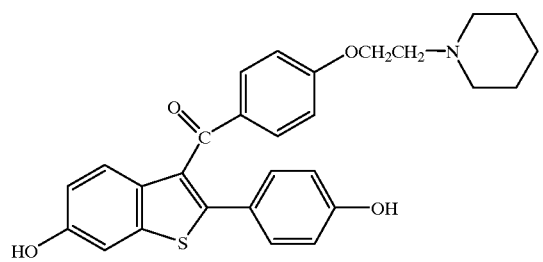

(I)

or a pharmaceutically acceptable salt or solvate thereof.

31. An article of manufacture of claim 30 wherein said label indicates an effective dose of the compound of formula I is between about 30 mg to about 200 mg/day.

32. An article of manufacture of claim 30 wherein said label indicates an effective dose of the compound of formula I is between about 50 mg to about 150 mg/day.

33. An article of manufacture of claim 30 wherein said label indicates an effective dose of the compound of formula I is between about 60 mg to about 120 mg/day.

34. An article of manufacture of claim 30 wherein said label indicates an effective dosage of the compound of formula I is about 60 mg/day.

35. An article of manufacture of claim 30 wherein said label indicates the term of administration is at least two years.

36. An article of manufacture of claim 30 wherein said label indicates the term of administration is chronic.

37. An article of manufacture of claim 30 wherein said compound is the hydrochloride salt thereof.

38. An article of manufacture of claim 30 where said breast cancer is de novo.

* * * * *